United States Patent
Fischer et al.

(10) Patent No.: US 6,306,206 B1
(45) Date of Patent: Oct. 23, 2001

(54) TEMPORARY DENTAL CEMENT COMPOSITIONS AND RELATED METHODS AND SYSTEMS

(75) Inventors: Dan E. Fischer, Sandy; Steven D. Jensen, South Jordan, both of UT (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

(21) Appl. No.: 09/478,550

(22) Filed: Jan. 6, 2000

(51) Int. Cl.⁷ ........................................ A61K 6/097
(52) U.S. Cl. .................... 106/35; 106/217.9; 433/228.1; 523/116
(58) Field of Search ......................... 433/228.1; 106/35, 106/217.9; 523/116

(56) References Cited

U.S. PATENT DOCUMENTS

| | | | |
|---|---|---|---|
| 3,741,926 | * 6/1973 | Jurecic | 106/35 |
| 3,837,865 | 9/1974 | Pellico | 106/35 |
| 4,161,410 | 7/1979 | Pellico | 106/35 |
| 4,288,355 | * 9/1981 | Anderson et al. | 106/35 |
| 4,375,968 | 3/1983 | Manhart | 433/217 |
| 4,547,531 | 10/1985 | Waknine | 523/116 |
| 4,872,936 | 10/1989 | Engelbrecht | 156/307.3 |
| 5,051,453 | 9/1991 | Okabayashi et al. | 523/116 |
| 5,063,257 | 11/1991 | Akahane et al. | 523/116 |
| 5,130,347 | 7/1992 | Mitra | 522/149 |
| 5,151,453 | 9/1992 | Ibsen et al. | 522/14 |
| 5,154,613 | 10/1992 | Cohen | 433/228.1 |
| 5,154,762 | 10/1992 | Mitra et al. | 106/35 |
| 5,234,971 | 8/1993 | Imai et al. | 523/113 |
| 5,367,002 | 11/1994 | Huang et al. | 523/116 |
| 5,512,611 | 4/1996 | Mitra | 523/116 |
| 5,520,725 | 5/1996 | Kato et al. | 106/35 |
| 5,534,562 | 7/1996 | Jensen et al. | 523/118 |
| 5,708,052 | 1/1998 | Fischer et al. | 523/116 |
| 5,709,548 | 1/1998 | Oxman et al. | 433/218 |
| 5,753,723 | 5/1998 | Chang et al. | 523/120 |
| 5,814,682 | 9/1998 | Rusin et al. | 523/116 |

* cited by examiner

*Primary Examiner*—C. Melissa Koslow
(74) *Attorney, Agent, or Firm*—Workman, Nydegger & Seeley

(57) ABSTRACT

A temporary dental cement composition temporarily affixes a dental prosthesis or appliance to a tooth or other dental substrate. The dental cement includes a mixture of: (i) an ion leaching agent; (ii) polycarboxylic acid; (iii) sugar; and (iv) water. The sugar is added in a sufficient amount that the ion leaching agent and polycarboxylic acid form a hardenable adhesive having an adhesive matrix which forms a relatively weak, temporary bond, as opposed to a permanent bond. The temporary cement composition is compatible with subsequent deposition of typical bonding materials, such as resin luting agents as well as non-resin permanent cements.

48 Claims, No Drawings

TEMPORARY DENTAL CEMENT COMPOSITIONS AND RELATED METHODS AND SYSTEMS

BACKGROUND OF THE INVENTION

1. The Field of the Invention

This application is directed to compositions which are particularly useful in dentistry. More particularly, this application is directed to two-part, temporary dental cements.

2. The Relevant Technology

Dental cements are well known in the art. Permanent dental cements are typically employed to adhere a dental appliance or prosthesis to a tooth which has been prepared to receive the prosthesis or appliance. Modern permanent dental cements are typically comprised of a powder/liquid mixture comprising: (i) a first component, or component "A," such as zinc oxide or glass ionomer silica; and (ii) a second component, or component "B," such as an aqueous solution of polyacrylic acid or phosphoric acid.

With the mixture of zinc oxide and aqueous polyacrylic acid, for example, an acid-base reaction occurs which forms a salt. The salt has a matrix which forms a strong bond between (i) a tooth; and (ii) a prosthesis or appliance. Typical permanent dental cements are also resistant to erosion in oral fluid and feature a low irritancy to tooth pulp.

When resins are employed as a permanent bonding material, the deposition of the final permanent bonding material is typically preceded by the application of a hydrophilic resin primer(s) to the tooth preparation. Bonding primers bond to the tooth surface, after which the permanent luting resin is bonded onto the bonding primer. The use of a bonding primer increases the overall adhesion of the permanent luting resin cement.

Although permanent dental cements are highly useful for a variety of different dental purposes, it is usually necessary to temporarily affix a prosthesis or appliance to a tooth, then later remove the prosthesis or appliance. For example, before mounting a permanent crown on a tooth which has been prepared to receive the crown, a dentist typically makes an impression of the tooth. The dentist then mounts a temporary crown on the tooth and sends the impression to a laboratory for manufacture of the permanent crown.

The temporary crown is held in place by a temporary dental cement until the permanent crown is prepared, upon which the temporary crown is removed. The permanent crown is then permanently affixed to the tooth through the use of permanent dental cement. Typical temporary dental cements are comprised of eugenol, rosins, pine gums, or tall oil mixed with zinc oxide.

Removal of temporary crowns from teeth is generally significantly easier than removal of permanent crowns from teeth due to the use of temporary dental cement, which is significantly weaker than permanent dental cement. Nevertheless, certain problems are associated with temporary cements currently used in dentistry.

For example, typical two-part temporary dental cements leave an insoluble, oily residue on a tooth and/or contaminate the underlying dentin and/or enamel so as to preclude quality definitive bonding, such as luting or another form of cementation. In addition to the annoyance of the film residue, the residue or contaminant on the tooth can contaminate a subsequent permanent bonding attempt because of incompatibility between the temporary cement contaminant and a bonding material placed on the residue, such as a bonding primer. The incompatibility between the residual temporary cement and the subsequently applied primer can interfere with the bonding of a permanent luting resin or another cement to the tooth.

This incompatibility is often caused by hydrophobic components within typical temporary dental cements which are incompatible with hydrophilic bonding materials, such as dental bonding primers, which are typically hydrophilic, at least upon initial placement upon the tooth surface before the primer is cured. Hydrophobic temporary cements which leave a residue on the tooth contaminate the bonding surface for the hydrophilic primers or other hydrophilic bonding materials. In addition, even some hydrophobic resins are caused not to polymerize by some hydrophobic temporary cement residues.

As a further complication, it is also often difficult to clean up typical hydrophobic temporary cements. These cements must generally be cleaned off with another hydrophobic composition, such as oil of orange, or another hydrophobic cleaner. Furthermore, typical hydrophobic temporary cements, such as eugenol, can also be irritating to nerve and pulp tissue.

Finally, typical temporary cements do not form a chemical bond with a dental substrate, but rather, use mechanical methods to retain a crown, for example, on a dental substrate. Consequently a drilled tooth cavity, for example, is suseptible to contamination and leakage of bacteria and other microorganisms into the cavity while the temporary cement is placed therein.

There is therefore a need in the art for an improved temporary dental cement. More specifically, there is a need in the art for a temporary dental cement which does not interfere with the bonding of a primer or permanent cement placed on a tooth after the removal of a temporary prosthesis or appliance from the tooth. There is also a need in the art for a temporary dental cement which readily cleans from a tooth, which does not irritate nerve and pulp tissue, and which does not permit microleakage of bacteria.

SUMMARY OF THE INVENTION

A two-part temporary dental cement of the present invention comprises an "A" component and a "B" component. The combined "A" and "B" components of the present invention form a cement which is temporary, is conveniently removed from a bonding surface when desired, and is compatible with permanent dental cements and a bonding primer/permanent cement system. Consequently, bonding material, such as a permanent cement and/or a bonding primer placed on the previous bonding site of the temporary cement is not significantly affected by the temporary cement. The temporary dental cement may be employed prior to deposition of permanent cement with or without the use of a bonding primer.

Component "A" comprises an ion leaching agent, while component "B" comprises polycarboxylic acid. The ion leaching agent of component "A" and the polycarboxylic acid of component "B" form a salt having a matrix which forms a bond between (i) a dental substrate; and (ii) a dental appliance (e.g., orthodontic devices) or prothesis (e.g., crowns and veneers).

The term "dental substrate" as used in the specification and the appended claims is defined to include tooth enamel, dentin, other tooth structures, crowns, veneers, fillings, and other materials and structures related to the repair and conditioning of teeth to which a prosthesis or appliance can be bonded. Water is also present, preferably as part of each of the "A" and "B" components. Components "A" and "B" are preferably each in a convenient syringe deliverable form.

One or more sugars is added, preferably, as a part of component "A". Sugar has a variety of advantages. First, sugar acts as a colloidal suspending agent to form a stable colloidal suspension from the ion leaching agent and water, preventing the settling of the ion leaching agent out of solution, and forming a syringe deliverable paste (i.e., a viscous liquid) for component "A". The syringe deliverability of the composition enables convenient delivery of both the "A" and "B" compositions.

Second, when the sugar-containing composition "A" is added to the composition "B", the sugar enables the formation of an adhesive matrix which is sufficient to achieve a bond which is a temporary bond, as opposed to a more secure permanent bond. The appropriate amount of sugar weakens the resulting adhesive matrix, yet allows the "A" and "B" materials to harden. Thus, the addition of sugar enables the composition "A" to be delivered in a syringe-deliverable form while nevertheless enabling the hardening of the mixed compositions "A" and "B". The sugar is added in a sufficient amount that the "A" and "B" components form a hardenable adhesive having an adhesive matrix which forms a relatively weak, temporary bond, as opposed to a permanent bond.

Third, sugars are hydrophilic. The sugar readily solubilizes in water and hence can be conveniently cleaned off a dental substrate with a water-based composition. In light of the addition of sugar, the temporary cement composition of the present invention cleans off more easily than oil or other hydrophobic temporary cements. In addition, the hydrophilic sugar does not significantly affect hydrophilic bonding materials, such as hydrophilic bonding primers and permanent cements, whereas previous hydrophobic temporary cements contaminate bonding sites.

The temporary cement composition is compatible with typical bonding materials such as bonding primers and/or permanent dental cements. For example, since the invented temporary cement comprises a polycarboxylic acid/ion leaching agent salt, the cement is compatible with typical permanent cements which comprise: (i) polycarboxylic acid or phosphoric acids and the like, and (ii) an ion leaching agent, such as cements comprising polyacrylic acid and zinc oxide, as well as bonding primer/luting resin systems.

Thus, following removal of a temporary crown, the temporary cement composition of the present invention cleans conveniently off a dental substrate with water based scouring agents, such as CONSEPSIS® SCRUB, produced by Ultradent Products, Inc. Nevertheless, as mentioned, the temporary cement composition is compatible with typical bonding primers and/or permanent dental cements. Consequently, even in the event fragments of the composition remain on a tooth following cleaning, the fragments do not significantly affect the bonding site, as opposed to previous temporary cements, which can contaminate bonding sites.

The sugar based temporary dental cement is also non-irritating to tooth nerve and pulp tissue. Furthermore, the temporary dental cement of the present invention also prevents or at least decreases the likelihood of leakage of bacteria and other microorganisms into a tooth cavity by forming a weak chemical adhesion, i.e., a temporary seal, between a dental substrate and a prosthesis or appliance bonded thereto.

These and other objects, features and advantages of the present invention will become more fully apparent from the following description and appended claims, or may be learned by the practice of the invention as set forth hereinafter.

DETAILED DESCRIPTION OF THE PREFERRED EMBODIMENTS

The two-part, temporary dental cement of the present invention comprises an "A" component and a "B" component. The "A" and "B" components are preferably each in the form of a paste (i.e., a viscous liquid) which, when mixed, harden into a temporary dental cement. The dental cement comprises sugar, which has a variety of different advantages, including colloidal suspending properties which promote syringe deliverability, matrix weakening properties which nevertheless allow matrix hardening, and water solubility, which promotes convenient clean up.

Following the removal of a temporary crown from a tooth or other dental substrate, any temporary cement of the present invention remaining can be conveniently scraped off with a dental tool and/or scoured off the substrate with rotating brushes or cups and a water-based abrasive slurry, e.g., CONSEPSIS® SCRUB, produced by Ultradent Products, Inc. Additionally, if needed, further cleaning is aided by the etching step during the bonding process.

Nevertheless, even if fragments of the composition remain on the dental substrate, a bonding material such as a permanent cement or hydrophilic primer placed on fragments or remnants of the temporary cement is compatible with the temporary cement. Thus, use of the temporary cement of the present invention does not significantly affect a permanent bonding site. Consequently, the combined "A" and "B" components of the present invention form a cement which is temporary and yet which is compatible with a bonding material placed on the bonding site of the temporary cement.

In one embodiment, component "A" comprises an ion leaching agent, while component "B" comprises polycarboxylic acid. Water is also included in the mixture, preferably in each of the "A" and "B" components. The ion leaching agent of component "A" and the polycarboxylic acid of component "B" form a salt having a matrix which forms a bond between: (i) a dental substrate such as a tooth; and (ii) a dental appliance or prothesis. Sugar may be added as part of either of the "A" or "B" components or as a separate "C" component, but is preferably part of the component which contains the ion leaching agent. Thus, sugar can act as a colloidal suspending agent to form a stable colloidal suspension for the ion leaching agent and water. This prevents the ion leaching agent from settling out of solution. The stability results in a syringe-deliverable paste for component "A. " The sugar is added in a sufficient amount that the "A" and "B" components form a hardenable adhesive having an adhesive matrix which forms a relatively weak, temporary bond, as opposed to a permanent-type bond.

Regardless of whether sugar is added as part of the "A" or "B" components or as a separate "C" component, sugar is preferably present in an amount of about 0.5% to about 35% by weight of the overall composition, more preferably about 2.5% to about 30% by weight of the overall composition, more preferably about 7.5% to about 20% by weight of the overall composition.

Fillers, lubricating agents and other ingredients may also be added to the cement composition to achieve a desired texture, viscosity, flow property, set hardness, and body. Typically, component "A" is contained in a container such as a syringe separate from component "B", which may also be stored in a syringe, for example, until it is desired to mix the components in a mixing bowl or syringe, for example.

Component "A" will now be discussed in additional detail. Component "A" is a composition which reacts with polycarboxylic acid to form a temporary dental cement. A preferred component "A" of the temporary cement of the present invention comprises: (i) an ion leaching agent; (ii) sugar; (iii) water; and, optionally (iv) a filler material such as fumed silica.

The ion leaching agent of component "A" is present in an amount sufficient to react with polycarboxylic acid to thereby form a hardenable adhesive composition. The sugar is present in an amount sufficient for the "A" and "B" compositions to form a temporary bond. Water is present in an amount sufficient to form an appropriate hardenable paste.

Examples of an ion leaching agent of the present invention useful in component "A" include metal oxides such as zinc oxide. Other possible ion leaching agents include magnesium oxide, calcium oxide, aluminum oxide, barium or strontium aluminosilicate glasses, other aluminosilicate glasses, and other agents which react with polycarboxylic acid to harden into a cement which is biocompatible within the oral cavity.

Filler, such as fumed silica can be employed in component "A" to achieve a desired viscosity. Fumed silica, however, is merely an example of a silicate or other filler which can be employed in the present invention. Other filler materials may alternatively be employed as viscosity modifying agents, such as aluminum oxides, silicas, and silicon carbides.

In light of the addition of the sugar, such as sorbitol, the combined "A" and "B" components form a hardenable cement. However, the addition of sugar ultimately results in a diluted, relatively weak adhesive matrix. As a mixed composition comprising: (i) component "A" containing sorbitol or another sugar; and (ii) component "B" sets, the composition hardens to form a temporary bond.

As mentioned, in addition to forming a relatively weak adhesive matrix, sorbitol and other sugars act as a colloidal suspending agent in composition "A". The suspending action of the sugar(s) causes zinc oxide, for example (or another leaching agent), and water to be suspended in a homogeneous mixture and then to bond in a homogeneous manner. By serving as a colloidal suspending agent within composition "A", the sugar promotes the syringe deliverability of composition "A". Thus, in light of the use of sorbitol or another sugar: (i) composition "A" is a stable, syringe-deliverable colloidal suspension; and (ii) the mixture of compositions "A" and "B" hardens, but features a relatively weak adhesive salt matrix.

A variety of different sugars may be employed in the present invention, such as in component "A". Examples 0f six-carbon sugars which are useful in the present invention as colloidal suspending agents and which allow combined components "A" and "B" to form a temporary dental cement include sorbitol, galactol, mannitol and mixtures and derivatives of the same. For example, in one embodiment, sorbitol is employed independently from other sugars. However, in another embodiment, a combination of sorbitol and mannitol, a combination or sorbitol galactol, or a combination of sorbitol and mannitol are employed in the temporary cement composition. Optionally, galactol or mannitol are employed independently from each other and/or other six-carbon sugars.

A preferred chemical formula for a six carbon sugar of the present invention is $C_6H_{14}O_6$. A preferred chemical formula for a five-carbon sugar employed in the invented temporary dental cement composition is $C_5H_{12}O_5$. An example of a useful five-carbon sugar comprises xylitol. Xylitol is particularly useful because it has an anticariogenic, antimicrobial effect in the present invention, as well as acting as a colloidal suspending agent and a matrix weakener and having the other benefits of sugars. However, a variety of different sugar compounds having five or six carbon atoms are useful in the present invention. The sugar added pursuant to the present invention is preferably sugar selected from the group consisting of: (i) five-carbon sugars; (ii) six-carbon sugars; and (iii) mixtures and derivatives thereof.

The proportions of the compositions in component "A" may vary. However, examples of ranges of the compositions given in percent by weight are provided as follows. In one embodiment, the sugar is present in an amount of at least 1% by weight of component "A", preferably at least 2.5% by weight of component "A". In another embodiment, sugar is present in an amount of about 1% to about 70% by weight of component "A", preferably about 5% to about 60% by weight of component "A", more preferably about 15% to about 40% by weight of component "A".

In one embodiment, water is present in an amount of about 1% to about 80% by weight of component "A", preferably about 5% to about 70% by weight of component "A", more preferably about 5% to about 30% by weight of component "A". In one embodiment, the ion leaching agent is present in an amount of about 5% to about 85% by weight of component "A", more preferably about 50% to about 75% by weight of component "A".

Component "B" will now be discussed in additional detail. A preferred component "B" of the present invention comprises (i) a polycarboxylic acid such as a polyacrylic acid; (ii) water; (iii) an optional lubricating agent; and (iv) an optional filler, such as fumed silica. Examples of polycarboxylic acid useful in the present invention include polyacrylic acid and polymethacrylic acid.

Lubricating agents act as a bond interface lubricant and serve to further weaken the adhesive matrix formed by (i) the ion leaching agent; (ii) polycarboxylic acid; and (iii) sugar. Lubricating agents, such as polyethylene glycol, polypropylene glycol, and/or other lubricants, can be employed in Composition "B" (or optionally, in Composition "A"). Specific examples of such lubricants include polyols such as polyethylene glycol 300 to 8000 molecular weight, propylene glycol, polypropylene glycol 300 to 8000 molecular weight, and others.

A filler, such as fumed silica can be employed in component "B" to achieve a desired viscosity. Fumed silica, however, is merely an example of a silicate or other filler which can be employed in the present invention. Other filler materials may alternatively be employed which act as viscosity modifying agents, such as aluminum oxides, silicas, and silicon carbides. The filler can enhance syringe deliverability and prevent runniness of the composition.

In one embodiment, polycarboxylic acid is present in an amount of about 1% to about 99% by weight of the composition of component "B", preferably about 5% to about 95% by weight of component "B", more preferably about 15% to about 85% by weight of component "B", and most preferably about 25% to about 75% by weight of component "B". In one embodiment, water is present in an amount of about 1% to about 99% by weight of the composition of component "B", preferably about 5% to about 95% by weight of component "B", more preferably about 15% to about 85% by weight of component "B", and most preferably about 25% to about 75% by weight of component "B". In one embodiment, the lubricating agent is present in an amount of about 0.5% to about 15% by weight of the composition of component "B", preferably about 1% to about 10% by weight of component "B", and most preferably about 5% to about 10% by weight of component "B".

The "A" and "B" components may be mixed in any stoichiometric ratio which forms a hardenable adhesive composition, such as equal proportions, for example, although a wide range of mixture proportions are available to achieve a hardenable adhesive.

In one embodiment, an antimicrobial agent is added to the composition. Examples of such antimicrobial agents to be added include: chlorhexidine, 1,1'-hexamethylene bis(5(p-chlorophenyl)biguanide), cetyl pyridinium chloride, benzalkonium chloride, cetyl pyridinium bromide, methyl 4-hydroxybenzoate and propylparaben (propyl p-hydroxybenzoate). The antimicrobial agent may be added in any suitable amount, but is preferably added in the amount of up to about 1% by weight of the overall cement composition, more preferably up to about 0.75 percent by weight of the overall cement composition, and most preferably up to about 0.5 percent by weight of the overall cement composition, for example.

The present invention also envisions the formation of a temporary cement composition comprising sugar which can be utilized as a temporary filling material. In one embodiment, this temporary filling material has the same or substantially the same amount of sugar and other ingredients as are in the foregoing described temporary cement compositions, but has a greater viscosity than cements deposited between dental substrates and temporary dental prosthesis or appliances. The viscosity may be increased, for example, through the addition of silica, such as fumed silica. Other filler materials may alternatively be employed as viscosity modifying agents, such as aluminum oxides, silicas, and silicon carbides. The temporary filling material can be employed, for example, when permanent fillings or crowns break or become dislodged from a tooth and immediate permanent replacement is unavailable or impractical.

One method for affixing a dental prosthesis or appliance to a tooth or other dental substrate comprises: (A) mixing (i) an ion leaching agent, (ii) polycarboxylic acid, (iii) sugar, and (iv) water to form a temporary dental cement composition; (B) depositing the temporary dental cement composition between a dental substrate and a dental prosthesis or appliance; and (C) allowing the temporary dental cement composition to harden.

When it is desired to replace the initial prosthesis or appliance with another prosthesis or appliance (e.g., a permanent crown), the method further comprises removing the initial prosthesis or appliance from the dental substrate and removing excess temporary cement from the dental substrate. The method further comprises: (A) providing a permanent bonding material, such as a polyacrylic/zinc oxide cement or a luting resin; (B) depositing the bonding material between the dental substrate and a second dental prosthesis or appliance (e.g., a permanent crown); and (C) allowing the bonding material to harden (e.g., through two-part chemical application or light curing).

In one embodiment, such as when a resin-based permanent cement is employed, before the final permanent bonding material is deposited between the substrate and the prosthesis or appliance, the method of affixing comprises (A) etching the substrate; (B) providing a hydrophilic bonding material comprising a bonding primer; (C) depositing the primer on the dental substrate; and (D) allowing the primer to harden (e.g., through light curing). The hydrophilic bonding primer is initially bonded to the dental substrate and allowed to harden, after which the permanent dental cement is bonded onto the bonding primer to thereby bond to the tooth.

In one embodiment, prior to the step of depositing the temporary dental composition between a dental substrate and a prosthesis or appliance, the method comprises: (i) depositing an aqueous solution of polycarboxylic acid in a first syringe and (ii) depositing a colloidal suspension of sugar, water and ion leaching agent in a second syringe. The compositions within respective syringes are then deposited into a common container and mixed, after which the mixed composition is deposited between a tooth or other dental substrate and a dental prosthesis or appliance. The common container may be the first or second syringe, or a separate, third syringe, for example, a mixing bowl, or another container.

In one embodiment, two separate syringes which deliver separate "A" and "B" materials are combined into a unified delivery device. One example of such a two-syringe device for delivering separate "A" and "B" materials is disclosed in U.S. Pat. No. 5,290,259 to Fischer, entitled "Double-Syringe Delivery System", which is incorporated herein in its entirety by reference.

An example of a kit for forming a composition which reacts with polycarboxylic acid to form a temporary dental cement comprises: (i) an ion leaching agent; (ii) sugar; and (iii) water. The kit preferably further contains a container, such as a syringe for containing the composition until it is desired to mix the composition with polycarboxylic acid.

An example of a kit for forming a temporary dental cement composition for temporarily affixing a dental prosthesis or appliance to a dental substrate such as a tooth comprises: (i) an ion leaching agent; (ii) polycarboxylic acid in an amount sufficient to react with the ion leaching agent to thereby form an adhesive composition; (iii) sugar; (iv) water in an amount sufficient amount to form a hardenable paste; and, preferably, (v) first and second containers, such as syringes for containing the "A" composition until it is desired to mix it with the "B" composition.

The present invention can be in the form of a powder (e.g., sugar and ion leaching agent) and a liquid (e.g., aqueous polycarboxylic acid) which combine to form the temporary dental cement of the present invention. However, as a major advantage of the present invention enabled through the use of sugar, both compositions "A" and "B" can be in a liquid form which combine to form the temporary cement composition, thus providing convenient syringe deliverbility. Furthermore, notwithstanding the liquid/liquid combination, the combined "A" and "B" mixture hardens sufficiently to form a bond, yet forms a temporary bond, rather than a permanent bond.

Examples of permanent cements which are useful in the present invention include, for example, polycarboxylic acid based permanent cements, glass ionomer cements, zinc phosphate cements, luting resins and a variety of different permanent dental cements.

A "reaction product" or "mixture product" is the product or products which result(s) elements of a composition are mixed.

EXAMPLES OF THE INVENTION

Examples of the invention will now be discussed with reference to the following tables and text.

Example 1 demonstrates an embodiment of a temporary dental cement of the present invention which is capable of forming a temporary bond between a tooth and a crown. Example 2 demonstrates that the temporary cement of the present invention does not significantly affect the bonding site of a tooth. Examples 3–5 are examples of additional formulas for temporary dental cements. A variety of other formulas may be employed according to the present invention, however.

Examples 6–15 demonstrate a variety of examples of formulas which do not successfully form temporary dental cements. Certain formulas are not capable of hardening into cements which form a bond while other formulas do not remain in solution. The sorbitol-containing composition of Example 1, on the other hand, remained in solution and hardened into a dental cement which formed a temporary bond which did not significantly affect an attempt to form a permanent bond.

The results of the tests are surprising and unexpected. Whereas sorbitol was successfully employed within a temporary dental cement, glycerin and other humectants failed to produce a successful temporary cement. These unexpected results highlight the uniqueness, novelty, and usefulness of the temporary cement of the present invention.

Example 1

Formation of Temporary Cement

According to Example 1, the ingredients of composition "A" of Table 1a were mixed to form a heavy paste.

TABLE 1a

COMPOSITION "A"

| Ingredient | Amount by weight of the composition |
| --- | --- |
| zinc oxide | 63% |
| distilled water | 10.5% |
| fumed silica | 2% |
| sorbitol | 24.5% |

The ingredients of composition "B" of Table 1b were also mixed to form a separate heavy paste.

TABLE 1b

COMPOSITION "B"

| Ingredient | Amount by weight of the composition |
| --- | --- |
| polyacrylic acid 2000 m.w. | 52% |
| distilled water | 28% |
| polyethylene glycol 600 | 8% |
| fumed silica | 12% |

The A and B paste compositions of respective Tables 1a and 1b were then mixed in equal proportions to form a temporary adhesive cement paste. The mixed composition was then applied to an extracted human molar which had been prepared to receive a temporary crown. The temporary crown was then mounted on the tooth such that the mixed composition hardened and formed a bond between the tooth and the crown. The tooth and crown were left for approximately 24 hours at 37° C. Next, an instron machine was employed to shear the temporary crown from the tooth.

The temporary crown was mounted on the tooth in accordance with the methods described in a U.S. patent application Ser. No. 09/467,666, which is entitled "Apparatus and Methods for Forming a Bond Strength Adherend", filed Dec. 15, 1999, assigned to Ultradent Products, Inc. The temporary crown was sheared from the tooth in accordance with the methods discussed in a U.S. patent application, Ser. No. 09/467,665, entitled "Apparatus and Methods for Testing Shear Bond Strength," filed on Dec. 15, 1999, assigned to Ultradent Products, Inc.

The cement formed a solid bond between the temporary crown and the tooth which snapped in a brittle breaking fashion when 6.1 pounds of tensile force were applied to remove the temporary crown. The cement thus exhibited the qualities of a successful and highly useful temporary cement.

Example 2

Control & Experimental Shear Tests to Evaluate Compatibility

First and second shear tests were performed to evaluate the compatibility of permanent bonding materials to human molars which have had the temporary cement of Example 1 bonded thereto. The first test was a control group test in which the adhesion of a permanent dental cement to ground molars was tested. The second test was an experimental group test in which the temporary cement of Example 1 was initially bonded to ground molars and then removed before the adhesion of a subsequently bonded permanent dental cement was tested.

In the control test, five human molars were ground flat. Each of the molars were then etched with ULTRAETCH® dental etchant (commercially available from Ultradent Products, Inc.), which contains 35% by weight phosphoric acid as the active ingredient. The hydrophilic PQ-1® dentin bonding primer (commercially available from Ultradent Products, Inc.) was then applied to each of the molars and light cured, after which a portion of Z-100® posterior composite acrylic resin permanent dental cement (commercially available from 3M Corporation) was bonded to the primer through light curing.

After the permanent dental cement cured, the molars were placed in water at 37° C. for 24 hours to simulate dental conditions in the mouth of a patient. Next, an instron machine was employed to shear the dental cement from each of the molars. The average force required to shear the permanent cement from each of the five teeth was 60.22 megapascals.

In the experimental test, compositions "A" and "B" of respective Tables 1a and 1b of Example 1 were formed, then mixed together to form a temporary dental cement. Small portions of the temporary dental cement were placed on five respective molars which had been ground flat. The temporary cement was then allowed to cure on the respective teeth, after which each molar was placed in water at 37° C. for 1 hour. The temporary cement was then removed from each tooth with a dental instrument. Each of the teeth were then etched with ULTRAETCH® primed with PQ-1®, and bonded with a portion of Z-100® posterior composite acrylic resin permanent dental cement in the same manner as the control test.

After the permanent dental cement cured, the molars were placed in water at 37° C. for 24 hours to simulate dental conditions in the mouth of a patient. Next, an instron machine was employed to shear the dental cement from the molars. The average force required to shear the permanent cement from each of the five teeth was 59.7 megapascals.

The force required to shear teeth initially receiving temporary dental cement was thus statistically the same as the force required to shear teeth which did not receive the temporary dental cement. The statistically insignificant differences in force (only 0.52 megapascals) may be attributed to laboratory error, variables in tooth strength among samples (e.g., size of dentinal tubules), and other variables typical in tooth bond testing.

The temporary dental cement of Example 1 thus either (i) cleans off teeth well enough that it does not leave fragments behind which prevent or weaken attempts to form a permanent bond; or (ii) is chemically compatible with a hydrophilic primer placed thereon. In either event, the placement of the temporary cement of the present invention on a dental substrate is compatible with the subsequent placement of a bonding material on the bonding site of the temporary cement.

Example 3

Hypothetical

According to Example 3, the ingredients of Table 3 are mixed to form a heavy paste.

TABLE 3

| Ingredient | Amount by weight of the composition |
| --- | --- |
| zinc oxide | 63% |
| distilled water | 12.5% |
| fumed silica | 2% |
| galactol | 22.50% |

The ingredients of composition "B" of Table 1b of Example 1 are mixed to form a separate heavy paste. The paste compositions of respective Tables 3 and 1b are mixed in equal proportions to form an adhesive temporary cement paste. The cement would be expected to exhibit the qualities of a successful and highly useful temporary cement.

Example 4

Hypothetical

According to Example 4, the ingredients of Table 4 are mixed to form a heavy paste.

TABLE 4

| COMPOSITION "A" | |
| --- | --- |
| Ingredient | Amount by weight of the composition |
| zinc oxide | 63% |
| distilled water | 10.5% |
| fumed silica | 2% |

TABLE 4

| COMPOSITION "A" | |
| --- | --- |
| Ingredient | Amount by weight of the composition |
| mannitol | 14.5% |
| sorbitol | 10% |

The ingredients of composition "B" of Table 1b of Example 1 are mixed to form a separate heavy paste. The paste compositions of respective Tables 4 and 1b are mixed in equal proportions to form an adhesive temporary cement paste. The cement would be expected to exhibit the qualities of a successful and highly useful temporary cement.

Example 5

Hypothetical

According to Example 5, the ingredients of Table 5 are mixed to form a heavy paste.

TABLE 5

| COMPOSITION "A" | |
| --- | --- |
| Ingredient | Amount by weight of the composition |
| zinc oxide | 63% |
| distilled water | 10.5% |
| fumed silica | 2% |
| galactol | 12% |
| sorbitol | 12.5% |

The ingredients of composition "B" of Table 1b of Example 1 are mixed to form a separate heavy paste. The paste compositions of respective Tables 5 and 1b are mixed in equal proportions to form an adhesive temporary cement paste. The cement would be expected to exhibit the qualities of a successful and highly useful temporary cement.

Example 6

Comparative

According to Example 6, the ingredients of Table 6 were mixed.

TABLE 6

| Ingredient | Amount by weight of the composition |
| --- | --- |
| propylene glycol | 36% |
| zinc oxide | 64% |

The ingredients of composition "B" of Table 1b were also mixed to form a separate heavy paste. The compositions of respective Tables 6 and 1b were then mixed in equal proportions. Upon mixing, a mass was formed which did not exhibit properties consistent with that of a temporary dental cement. The mixed composition did not become hard enough to form an adhesive solid.

Example 7

Comparative

According to Example 7, the ingredients of Table 7 were mixed.

TABLE 7

| COMPOSITION "A" | |
| --- | --- |
| Ingredient | Amount by weight of the composition |
| glycerin | 30% |
| zinc oxide | 70% |

The ingredients of composition "B" of Table 1b were also mixed to form a separate heavy paste. The compositions of respective Tables 7 and 1b were then mixed in equal proportions. Upon mixing, a mass was formed which did not exhibit properties consistent with that of a temporary dental cement. The mixed composition did not become hard enough to form an adhesive solid.

Example 8

Comparative

According to Example 8, the ingredients of Table 8 were mixed.

TABLE 8

COMPOSITION "A"

| Ingredient | Amount by weight of the composition |
|---|---|
| polyethylene glycol 300 | 40% |
| zinc oxide | 60% |

The ingredients of composition "B" of Table 1b were also mixed to form a separate heavy paste. The compositions of respective Tables 8 and 1b were then mixed in equal proportions. Upon mixing, a mass was formed which did not exhibit properties consistent with that of a temporary dental cement. The mixed composition remained as a jelly-like mass and never hardened.

Example 9

Comparative

According to Example 9, the ingredients of Table 9 were mixed.

TABLE 9

COMPOSITION "A"

| Ingredient | Amount by weight of the composition |
|---|---|
| polyethylene glycol 600 | 50% |
| zinc oxide | 50% |

The ingredients of composition "B" of Table 1b were also mixed to form a separate heavy paste. The compositions of respective Tables 9 and 1b were then mixed in equal proportions. Upon mixing, a mass was formed which did not exhibit properties consistent with that of a temporary dental cement. The mixed composition remained as a jelly-like mass and never hardened.

Example 10

Comparative

According to Example 10, the ingredients of Table 10 were mixed.

TABLE 10

COMPOSITION "A"

| Ingredient | Amount by weight of the composition |
|---|---|
| water | 34% |
| xanthan gum | 1% |
| zinc oxide | 65% |

The ingredients of composition "B" of Table 1b were also mixed to form a separate heavy paste. The compositions of respective Tables 10 and 1b were then mixed in equal proportions. Upon mixing, a mass was formed which did not exhibit properties consistent with that of a temporary dental cement. The mixture of Table 10 did not form a homogeneous paste. Over time, zinc oxide separated from the aqueous xanthan gum solution.

Example 11

Comparative

According to Example 11, the ingredients of Table 11 were mixed.

TABLE 11

COMPOSITION "A"

| Ingredient | Amount by weight of the composition |
|---|---|
| water | 24% |
| xanthan gum | 1% |
| zinc oxide | 65% |
| polyethylene glycol | 10% |

The ingredients of composition "B" of Table 1b were also mixed to form a separate heavy paste. The compositions of respective Tables 11 and 1b were then mixed in equal proportions. Upon mixing, a mass was formed which did not exhibit properties consistent with that of a temporary dental cement. The mixed composition remained as a jelly-like mass and never hardened.

Example 12

Comparative

According to Example 12, the ingredients of Table 12 were mixed.

TABLE 12

COMPOSITION "A"

| Ingredient | Amount by weight of the composition |
|---|---|
| polypropylene glycol 300 | 40% |
| zinc oxide | 60% |

The ingredients of composition "B" of Table 1b were also mixed to form a separate heavy paste. The compositions of respective Tables 12 and 1b were then mixed in equal proportions. Upon mixing, a mass was formed which did not exhibit properties consistent with that of a temporary dental cement. The mixed composition remained as a jelly-like mass and never hardened.

Example 13

Hypothetical

According to Example 13, the ingredients of Table 13 are mixed.

TABLE 13

COMPOSITION "A"

| Ingredient | Amount by weight of the composition |
|---|---|
| water | 40% |
| zinc oxide | 60% |

The ingredients of composition "B" of Table 1b are also mixed to form a separate heavy paste. The compositions of respective Tables 13 and 1b are then mixed in equal proportions. Upon mixing, a mass is formed which does not exhibit properties consistent with that of a temporary dental cement. The mixture of Table 13 does not form a homogeneous paste. Over time, zinc oxide separates from the water.

Example 14

Hypothetical

According to Example 14, the ingredients of Table 14 are mixed.

TABLE 14

| COMPOSITION "A" | |
| --- | --- |
| Ingredient | Amount by weight of the composition |
| 1-butanol | 30% |
| zinc oxide | 70% |

The ingredients of composition "B" of Table 1b are also mixed to form a separate heavy paste. The compositions of respective Tables 14 and 1b are then mixed in equal proportions. Upon mixing, a mass is formed which does not exhibit properties consistent with that of a temporary dental cement. The mixture of Table 14 does not form a homogeneous paste. Over time, zinc oxide separates from the butanol.

Example 15

Hypothetical

According to Example 15, the ingredients of Table 15 are mixed.

TABLE 15

| COMPOSITION "A" | |
| --- | --- |
| Ingredient | Amount by weight of the composition |
| 1-Hexanol | 38% |
| zinc oxide | 62% |

The ingredients of composition "B" of Table 1b are also mixed to form a separate heavy paste. The compositions of respective Tables 15 and 1b are then mixed in equal proportions. Upon mixing, a mass is formed which does not exhibit properties consistent with that of a temporary dental cement. The mixed composition does not become hard enough to form an adhesive solid.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for forming a temporary dental composition, the method comprising:
   mixing (i) at least one ion leaching agent;
   (ii) at least one polycarboxylic acid;
   (iii) at least one sugar selected from the group consisting of five-carbon sugars, six-carbon sugars, and mixtures and derivatives thereof; and
   (iv) water to form a temporary dental composition which hardens in a manner such that it can be removed when desired,
   wherein the at least one sugar is present in an amount greater than 0.5% by weight of the temporary dental composition.

2. A method as recited in claim 1, wherein the ion leaching agent comprises zinc oxide.

3. A method as recited in claim 1, wherein the sugar comprises at least one sugar having a chemical formula of $C_6H_{14}O_6$.

4. A method as recited in claim 1, wherein the sugar comprises sorbitol.

5. A method as recited in claim 1, wherein the sugar comprises a compound selected from the group consisting of mannitol and galactol, and mixtures and derivatives thereof.

6. A method as recited in claim 1, wherein the polycarboxylic acid comprises at least one polyacrylic acid.

7. A method for forming a temporary dental composition, comprising:
   mixing a component "A" comprising a mixture of:
   (i) at least one ion leaching agent, and
   (ii) at least one sugar selected from the group consisting of five-carbon sugars, six-carbon sugars, and mixtures and derivatives thereof,
   wherein the at least one sugar is present in an amount of at least 1% by weight of component "A"; and
   a component "B" comprising an aqueous solution of at least one polycarboxylic acid to form a temporary dental composition which hardens in a manner such that it can be removed when desired.

8. A method as recited in claim 7, wherein the sugar is present in an amount of 1% to about 70% by weight of component "A", water is present in an amount of about 1% to about 80% by weight of component "A", and the ion leaching agent is present in an amount of about 5% to about 85% by weight of component "A".

9. A method as recited in claim 7, wherein the sugar is present in an amount of about 5% to about 60% by weight of component "A", water is present in an amount of about 5% to about 70% by weight of component "A", and the ion leaching agent is present in an amount of about 5% to about 85% by weight of component "A".

10. A method as recited in claim 7, wherein the sugar is present in an amount of about 15% to about 40% by weight of component "A", water is present in an amount of about 5% to about 30% by weight of component "A", and the ion leaching agent is present in an amount of about 50% to about 75% by weight of component "A".

11. A method as recited in claim 7, wherein the polycarboxylic acid is present in an amount of about 1% to about 99% by weight of component "B" and water is present in an amount of about 1% to about 99% by weight of component "B".

12. A method as recited in claim 7, wherein the polycarboxylic acid is present in an amount of about 25% to about 75% by weight of component "B" and water is present in an amount of about 25% to about 75% by weight of component "B".

13. A method as recited in claim 7, wherein component "A" is in the form of a powder.

14. A method as recited in claim 7, wherein component "A" is in the form of a liquid.

15. A method for treating a dental substrate, comprising:
   mixing (i) at least one ion leaching agent; (ii) at least one polycarboxylic acid; (iii) at least one sugar selected from the group consisting of five-carbon sugars, six-carbon sugars, and mixtures and derivatives thereof; and (iv) water to form a temporary dental cement composition which hardens in a manner such that it can be removed when it is desired to replace a temporary prosthesis or appliance with a permanent prosthesis or appliance, wherein the sugar is present in an amount of about 2.5% to about 30% by weight of the temporary dental cement composition;
   depositing the temporary dental cement composition between a dental substrate and a dental prosthesis or appliance; and allowing the temporary dental cement composition to harden.

16. A method as recited in claim 15, further comprising: (i) depositing an aqueous solution of at least one polycarboxylic acid from a first syringe; and (ii) depositing a colloidal suspension comprising at least one sugar, water, and at least one ion leaching agent from a second syringe prior to depositing the temporary dental cement composition between a dental substrate and a dental prosthesis or appliance.

17. A method as recited in claim 15, further comprising removing the dental prosthesis or appliance.

18. A method as recited in claim 15, further comprising:
removing the dental prosthesis or appliance;
providing at least one hydrophilic bonding material; and
depositing the hydrophilic bonding material on the dental substrate.

19. A composition which reacts with polycarboxylic acid to form dental composition for temporary use, the composition comprising:
at least one ion leaching agent;
water; and
at least one sugar selected from the group consisting of five-carbon sugars, six-carbon sugars, and mixtures and derivatives thereof,
wherein the sugar is present in an amount of at least 1% by weight of the composition.

20. A composition as recited in claim 19, wherein the sugar comprises a compound selected from the group consisting of mannitol and galactol, and mixtures and derivatives thereof.

21. A composition as recited in claim 19, wherein the composition comprises a syringe deliverable paste.

22. A composition as recited in claim 19, wherein the sugar acts as a colloidal suspending agent, to form a colloidal suspension for the ion leaching agent and water.

23. A composition as recited in claim 19, wherein the sugar is present in an amount of about 15% to about 40% by weight of the composition.

24. A composition which reacts with polycarboxylic acid to form a dental composition for temporary use, the comprising the mixture product of:
at least one ion leaching agent in an amount sufficient to react with the polycarboxylic acid;
water; and
at least one sugar, wherein the sugar comprises a compound selected from the group consisting of five-carbon sugars, six-carbon sugars, and mixtures and derivatives thereof,
wherein the sugar is present in an amount of at least 1% by weight of the composition.

25. A multi-part system for forming a dental composition for temporary use, the system comprising:
at least one ion leaching agent;
an aqueous solution of at least one polycarboxylic acid in an amount sufficient to react with the ion leaching agent; and
at least one six-carbon sugar in an amount sufficient to enable the temporary dental composition formed from the system to be removed when desired and in order for the sugar to be present in an amount greater than 0.5% by weight of the temporary dental composition.

26. A multi-part system as recited in claim 25, wherein the six-carbon sugar is added as a composition with the ion leaching agent.

27. A multi-part system as recited in claim 25, wherein the six-carbon sugar is added as a composition with the polycarboxylic acid solution.

28. A multi-part system as recited in claim 25, wherein the six-carbon sugar is added as a composition with the ion leaching agent, and wherein the sugar is present in an amount of about 2.5% to about 30% by weight of the temporary dental composition.

29. A system for forming a temporary dental cement composition for temporarily affixing a dental prosthesis or appliance to a dental substrate, the system comprising:
a first composition comprising a colloidal suspension of at least one ion leaching agent, water and at least one sugar selected from the group consisting of five-carbon sugars, six-carbon sugars, and mixtures and derivatives thereof, wherein the sugar is present in the first composition in an amount of about 5% to about 60% by weight; and
a second composition comprising an aqueous solution of at least one polycarboxylic acid in an amount sufficient to react with the first composition to thereby form a hardenable adhesive composition; wherein the first composition and the second composition are each present in sufficient amounts to form a temporary dental cement composition when the first and second compositions are mixed, such that a temporary dental cement composition formed by the combination of the first and second compositions can be removed when it is desired to replace a temporary prosthesis or appliance with a permanent prosthesis or appliance.

30. A system as recited in claim 29, wherein the sugar comprises xylitol.

31. A method as recited in claim 1, further comprising adding a filler material to the temporary dental composition.

32. A method as recited in claim 1, wherein the sugar is present in an amount of about 2.5% to about 30% by weight of the temporary dental composition.

33. A method as recited in claim 1, wherein sugar is present in an amount of about 7.5% to about 20% by weight of the temporary dental composition.

34. A method as recited in claim 7, wherein the temporary dental composition can temporarily affix a dental prosthesis or appliance to a dental substrate and wherein the sugar is present in an amount of at least 2.5% by weight of component "A".

35. A composition as recited in claim 19, wherein the sugar is present in an amount of at least 2.5% by weight of the composition which reacts with polycarboxylic acid.

36. A composition as recited in claim 19, wherein the sugar is present in an amount of about 5% to about 60% by weight of the composition which reacts with polycarboxylic acid.

37. A composition as recited in claim 24, wherein the sugar is present in an amount of at least 2.5% by weight of the composition which reacts with polycarboxylic acid.

38. A composition as recited in claim 24, wherein the sugar is present in an amount of about 5% to about 60% by weight of the composition which reacts with polycarboxylic acid.

39. A system as recited in claim 25, wherein sugar is present in an amount of about 2.5% to about 30% by weight of the temporary dental composition.

40. A system as recited in claim 25, wherein sugar is present in an amount of about 7.5% to about 20% by weight of the temporary dental composition.

41. A system as recited in claim 29, further comprising first and second syringes for containing the respective first and second compositions, until it is desired to mix the first and second compositions.

42. A method for affixing a temporary dental composition to a dental substrate, comprising:
    mixing (i) an ion leaching agent; (ii) polycarboxylic acid; (iii) sugar selected from the group consisting of five-carbon sugars, six-carbon sugars, and mixtures and derivatives thereof; and (iv) water to form a temporary dental composition which hardens in a manner such that it can be removed when desired, wherein sugar is present in an amount of about 2.5 % to about 30% by weight of the overall temporary dental composition;
    depositing the temporary dental composition onto a dental substrate; and
    allowing the temporary dental composition to harden.

43. A method as recited in claim 42, further comprising a filler material.

44. A method as recited in claim 42, wherein sugar is present in an amount of about 7.5% to about 20% by weight of the overall temporary dental composition.

45. A method for forming a temporary dental composition which can temporarily affix a dental prosthesis or appliance to a dental substrate, comprising:
    mixing (i) at least one ion leaching agent;
    (ii) at least one polycarboxylic acid;
    (iii) at least one sugar selected from the group consisting of five-carbon sugars, six-carbon sugars, and mixtures and derivatives thereof; and
    (iv) water to form a temporary dental cement composition which hardens in a manner such that it can be removed when it is desired to replace a temporary prosthesis or appliance with a permanent prosthesis or appliance, wherein the sugar comprises a compound selected from the group consisting of mannitol and galactol, and mixtures and derivatives thereof.

46. A method for forming a temporary dental composition which can temporarily affix a dental prosthesis or appliance to a dental substrate, comprising:
    mixing a component "A" comprising a mixture of at least one ion leaching agent and at least one sugar selected from the group consisting of five-carbon sugars, six-carbon sugars, and mixtures and derivatives thereof; and
    a component "B" comprising an aqueous solution of at least one polycarboxylic acid to form a temporary dental cement composition which hardens in a manner such that it can be removed when it is desired to replace the temporary prosthesis or appliance with a permanent prosthesis or appliance, wherein component "A" is provided in the form of a powder.

47. A composition which reacts with polycarboxylic acid to form a temporary dental cement, the composition comprising:
    at least one ion leaching agent in an amount sufficient to react with at least one polycarboxylic acid;
    water; and
    at least one sugar in an amount sufficient to allow the ion leaching agent and polycarboxylic acid to form a temporary dental cement which hardens in a manner such that it can be removed when desired,
    wherein the sugar is selected from the group consisting of mannitol and galactol, and mixtures and derivatives thereof.

48. A composition which reacts with polycarboxylic acid to form a temporary dental cement, the composition comprising:
    at least one ion leaching agent in an amount sufficient to react with the polycarboxylic acid;
    water; and
    at least one sugar in an amount sufficient to allow the ion leaching agent and polycarboxylic acid to form a temporary dental cement which hardens in a manner such that it can be removed when desired,
    wherein the sugar is selected from the group consisting of: (i) five-carbon sugars; (ii) six-carbon sugars, and (iii) mixtures and derivatives thereof,
    wherein the sugar acts as a colloidal suspending agent, to form a colloidal suspension for the ion leaching agent and water.

* * * * *

UNITED STATES PATENT AND TRADEMARK OFFICE
CERTIFICATE OF CORRECTION

PATENT NO. : 6,306,206 B1
DATED : October 23, 2001
INVENTOR(S) : Dan E. Fischer, Steven D. Jensen and Cornelis H. Pameijer It is certified that error appears in the above-identified patent and that said Letters Patent is hereby corrected as shown below:

<u>Title page,</u>
Under Inventors, insert -- Cornelis H. Pameijer, Simsbury, CT --

<u>Column 5,</u>
Line 58, after "sorbitol" insert -- and --
Line 59, after "combination of" change "sorbitol" to -- galactol --

Signed and Sealed this

Twenty-first Day of May, 2002

Attest:

Attesting Officer

JAMES E. ROGAN
Director of the United States Patent and Trademark Office